(12) United States Patent
McMillen et al.

(10) Patent No.: US 6,900,894 B2
(45) Date of Patent: May 31, 2005

(54) APPARATUS AND METHOD FOR MEASURING DOSE AND ENERGY OF ION IMPLANTATION BY EMPLOYING REFLECTIVE OPTICS

(75) Inventors: James A. McMillen, Foster City, CA (US); Evan Grund, San Jose, CA (US)

(73) Assignee: Process Diagnostics, Inc., Sunnyvale, CA (US)

( * ) Notice: Subject to any disclaimer, the term of this patent is extended or adjusted under 35 U.S.C. 154(b) by 394 days.

(21) Appl. No.: 09/991,215

(22) Filed: Nov. 16, 2001

(65) Prior Publication Data

US 2002/0080356 A1 Jun. 27, 2002

Related U.S. Application Data

(60) Provisional application No. 60/249,599, filed on Nov. 16, 2000.

(51) Int. Cl.[7] .............................................. G01N 21/55
(52) U.S. Cl. ...................................................... 356/445
(58) Field of Search ................................. 356/445–446, 356/630, 243.4

(56) References Cited

U.S. PATENT DOCUMENTS 4,682,206 A  *  7/1987  Tsuya et al. ................... 257/64
6,373,576 B1  *  4/2002  Yang .......................... 356/445
6,620,632 B2  *  9/2003  Koveshnikov et al. ........ 438/14

FOREIGN PATENT DOCUMENTS

GB            2339069        * 12/2000

* cited by examiner

Primary Examiner—Zandra V. Smith
(74) Attorney, Agent, or Firm—Bo-In Lin

(57) ABSTRACT

This invention discloses an apparatus for measuring an ion-implantation ion energy and/or dosage. The apparatus includes a scanning densitometer for measuring a reflected light from a monitor substrate. The apparatus further uses a monitor substrate. A thin film is supported on the monitor substrate wherein the thin film has an optical characteristic that is sensitive to the ion-implantation. The apparatus further includes a light source for projecting a measuring beam onto the monitor substrate for generating a reflected light. The apparatus also includes a bare silicon substrate for measuring a full scale reflected light represented by I0 reflected from the bare silicon substrate with the light source projecting a full scale light onto the bare silicon substrate. The apparatus further has a light source control means for controlling the light source to project the full scale light onto a plurality of points on the monitor substrate before and after an ion implantation for obtaining reflection intensities I' and I". The apparatus further includes an ion-implantation measurement controller for controlling the apparatus and for calculating the implantation energy and/or dosage from the reflected light from the monitor substrate and displaying implant profile data.

17 Claims, 5 Drawing Sheets

APPARATUS AND METHOD FOR MEASURING DOSE AND ENERGY OF ION IMPLANTATION BY EMPLOYING REFLECTIVE OPTICS

This Application is a Formal Application and claims a Priority Date of Nov. 16, 2000, benefited from a previously filed Provisional Application 60/249,599 by the same Applicants of this Application.

BACKGROUND OF THE INVENTION

1. Field of the Invention

This invention relates generally to apparatus and method used for ion implant dose and energy measurement. Particularly, this invention relates to a novel apparatus and method to perform a more accurate implant dose and/or energy measurement by applying a reflective measurement technique implemented with an optically dose-sensitive layer with measurements scaled to a referenced reflection without the dose-sensitive layer.

2. Description of the Prior Art

Precise measurement of dose and/or energy of ion implantation has become a challenge to those of ordinary skill in the art of integrated circuit (IC) manufacture. Particularly, as smaller and denser device geometry on integrated circuit (IC) chips are now built by the microelectronics industry for achieving increasing amounts of computing power. Specifically, the advent of denser, larger-scale integration has placed greater demand on the precise dopant concentration and uniform distribution. For example, as the circuit density has increased, designers have used lower operating voltages for complex circuits such as microprocessors in order to limit power dissipation and operating temperatures. The lower operating voltages requires more precision in the CMOS transistor switching threshold voltage (Vt). Ion implantation is now used for precisely setting the threshold voltage Vt. Limitations and difficulties to precisely measure the dose and energy of ion implantation at low dose levels would also cause limitations to further miniaturize and limit the manufacturing yields of high performance integrated circuits.

Referring to FIGS. 1A to 1C for a transmission technique applied to measure the dose and/or energy of an ion implantation. FIG. 1A shows a beam of light emitted from a light source project to a light detector that is focused to a small area in the beam path. FIG. 1B shows a film inserted at the focal point in the beam path. The light intensity is reduced with the film inserted at the focal point. Measurement of the light intensity at multiple points of the thin film is employed to develop a map of ion implant dose. At each point, the optical density of the film is determined by taking the logarithm of the ratio of the light intensity without the film to the light intensity with the film. As that shown in FIG. 1C, the film is supported on a glass or quartz substrate that is ground to a shape of a wafer normally used by the ion implanter for IC production. The light beam intensities at multiple points are measured before and after the ion implantation. The optical density changes are determined at each measurement site and a comparison is made with the known density changes from known implantation doses at specific energies or known energies at specific doses to determine the dose or energy of implantation for each measurement site.

The transmission measurement technique employed in the prior art method has a disadvantage due to requirement of using a transparent substrate. Possible contamination or damages of the transparent substrate can cause measurement errors. In the case when a glass substrate is broken, major expenses, manpower and loss of equipment productivity must be involved to remove the broken pieces. Since the ion implanter and all the associated machines are set up to handle silicon substrate, the use of glass or quartz substrates adds to the complexities of the material handling processes.

Therefore, a need still exists in the art of semiconductor industries to provide novel and improved apparatus and method for ion implant dose and energy measurements to overcome the limitations and difficulties now faced by those of ordinary skill in the art. It is desirable that the measurement techniques are compatible with the standard manufacture processes of integrated circuit such that minimum disruptions and adverse impacts would arise from using these novel measurement procedures. It is further desirable that the apparatus and sample substrate used for dose and energy measurements can be employed with ion beams provided from the implanter within the regular range of IC device manufacture. Further adjustment of the implanter energy and dose rate is not required and better measurement precision can also be achieved when ions beams of same range of energies, same dose rate and same implanting times are applied for production implantation and for implantation dose measurements.

SUMMARY OF THE PRESENT INVENTION

It is the object of the present invention to provide a new and improved apparatus and method to more rapidly and precisely carry out an ion-implantation dosage measurement with minimum disruptions to the standard manufacturing processes of the integrated circuit such that the above-mentioned problems and difficulties can be overcome.

Specifically, it is an object of the present invention to present a new and improved method and apparatus for carrying implantation dosage measurement by applying a reflective measurement technology. A monitoring substrate is employed for implantation dosage measurement by forming a thin film on a silicon substrate wherein the thin film has an optical property sensitive to an implantation dosage. Measurements of optical reflection intensity are performed before an implantation. Then a post implantation reflection intensity is performed and a set of reflection intensity differences are calculated. The differences of reflection intensities at many point on the monitoring substrate are then applied to determine an ion implantation dosage profile.

Another object of the present invention is to provide a new and improved apparatus and method for carrying out the implantation dosage measurement using standard equipment and processes to minimize disruptions and changes to the regular IC manufacture procedures. This is achieved by using a silicon monitor substrate deposited with thin film and implanted using standard implanter. The thin film deposition and reflection intensity measurements can be conveniently incorporated with regular IC manufacture processes using common equipment and processes with minimum changes to prevent adverse impacts to the standard manufacturing processes.

Briefly, in a preferred embodiment, the present invention discloses an apparatus for measuring an ion-implantation dosage. The apparatus includes a scanning densitometer for measuring a reflected light from a monitor substrate. The apparatus further uses a monitor substrate. A thin film is supported on the monitor substrate wherein the thin film has an optical characteristic that is sensitive to the ion-implantation-dosage. The apparatus further includes a light source for projecting a measuring beam onto the monitor substrate for generating a reflected light. The apparatus also includes a bare silicon substrate for measuring a full scale reflected light represented by I0 reflected from the bare silicon substrate with the light source projecting a full scale light onto the bare silicon substrate. The apparatus further has a light source control means for controlling the light source to project the full-scale light onto a plurality of points on the monitor substrate before and after an ion implantation for obtaining an implantation dosage profile. The apparatus further includes an ion-implantation dosage-measurement controller for controlling the apparatus and for calculating the implantation dosage from the reflected light from the monitor substrate.

This invention further discloses a method for measuring an ion-implantation dosage. The method includes a step of forming a thin film with an optical characteristic sensitive to an ion-implantation dosage. The method further includes another step of measuring a change of the optical characteristic after an ion implantation for calculating the ion-implantation dosage.

These and other objects and advantages of the present invention will no doubt become obvious to those of ordinary skill in the art after having read the following detailed description of the preferred embodiment, which is illustrated in the various drawing figures.

DETAILED DESCRIPTION OF THE PREFERRED EMBODIMENT

Figure 1A:
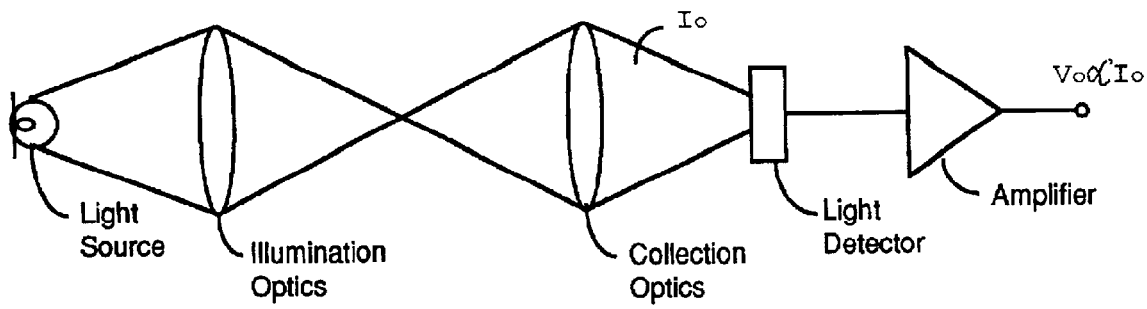
FIGS. 1A to 1C are diagrams for showing a conventional technique using transmission method to measure the dose and/or energy of an ion implantation.
Figure 1B:
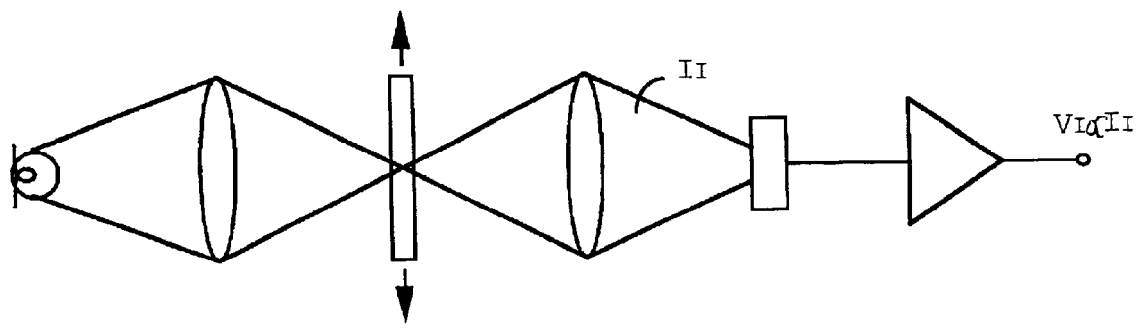
Figure 1C:
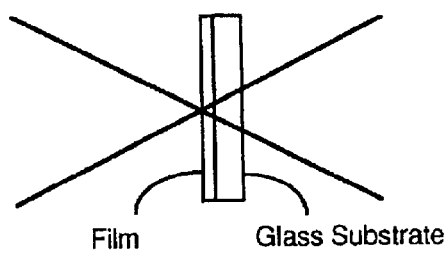
Figure 2A:
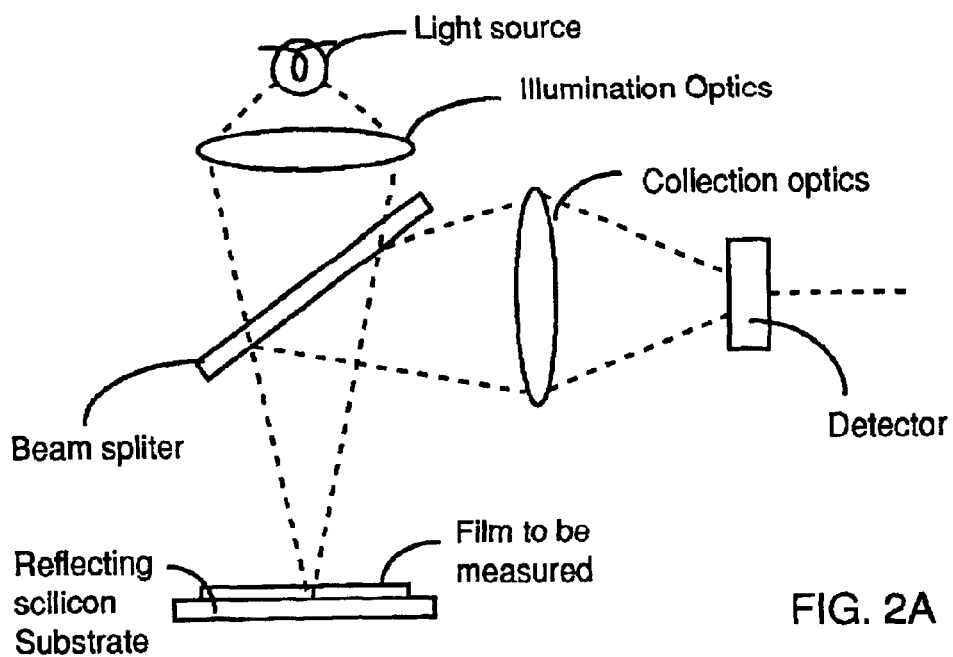
FIG. 2A for an optical system for performing an ion implant dose and/or energy measurement using a reflected light beam.

Referring to FIG. 2A for an optical system for performing an ion implant dose and/or energy measurement using a reflected light beam. A light beam emitted from a light source such as a light emitting diode (LED) light source 110 is collected and focused by an illuminating optics 115 that can a collecting lens or a set of lenses, to projected onto a 50—50 beam splitter 120. Half (50%) of the light beam is reflected to the left side of the system by the splitter 120. And, another half (50%) of the light is transmitted through the beam splitter 120 and focused on a small spot on the surface of a dose and energy sensitive film 125-f covering a substrate 125. The light projected onto the surface of the substrate 125 is reflected back to the beam splitter 120 with half of the light reflected and focused by a collecting optics, e.g., a convex lens 130 onto a light detector 135.

The dose and energy sensitive film 125-f has the properties to develop an easily measurable optical characteristic change when bombarded with ions. The optical characteristic change is developed gradually over a range of ion implant dose and energy such that a degree of the optical characteristic change can be measured to achieve the purpose of correlating to a corresponding dose and energy of ion implantation. Therefore, the thin film 125-f needs to be sensitive to the implanting ions. Furthermore, to prevent the implant dose-energy measurement to cause unnecessary disruption and inconvenience to the manufacture processes, it is preferred that the film 125-f can be applied and handled with standard semiconductor processing equipment and procedures. In this invention, the thin film 125-f is a mixture of a dye molecules with a weak covalent bond and one or more polymers that may be dispensed for wafer coating with solvent. The resulting film 125-f coated over the substrate 125 has optical properties of a semitransparent film, with the dye molecules uniformly dispersed throughout the entire layer. The dye in the film has an optical response to various amounts of ion implantation. Specifically, during an implantation process, some of the covalent bonds of the dye molecules are broken. The breaking of the covalent bonds occurs through a known process of commonly referred to as a process of "heterogeneous cleavage". Before cleavage the dye molecule is optically nearly transparent, while after cleavage two molecules result with one of them able to absorb light of a particular wavelength range. While there are a number of dyes known to chemists that exhibit this property, for this invention, a group of dyes that has covalent bonds that are easily broken is chosen. This group of dyes is quite sensitive to the bombardment of ion species when bombarded with ion energies typically in an ion energy range implemented for the semiconductor ion implanters.

The selected group of dyes for this invention when used for implant dose-energy measurement is mixed with roughly equal parts of one or more polymers and solvents. The mixture can be coated on silicon wafers with equipment and processes very similar to coating of a photoresist. Since the application of the photoresist is a common and well-known semiconductor processing procedure, coating of this mixture over the substrate can be conveniently processed. The film thickness is in a thickness range that can fully absorb and stop the ions with kinetic energies of over one million electron volts from traveling through the film. The solvent is evaporated to produce the finished film that is largely of uniform thickness. The polymers in the film also provide a stabilizing matrix that prevents dye module components from recombining after cleavage. Typical layer structure is formed with silicon wafers coated with a layer of 1 to 10 microns of the sensitive film by a spin coating process. It is sometimes desirable to have the bare silicon wafers pre-coated with 500 to 1000 angstroms of silicon dioxide to provide a transparent surface over the silicon that is scratch resistant and has good adhesive properties for the said film. In practice the film is exposed during the measurement process and then is removed from the wafer and a new layer of film is deposited, thus allowing the substrate wafer to be reused many times.

Figure 2B:
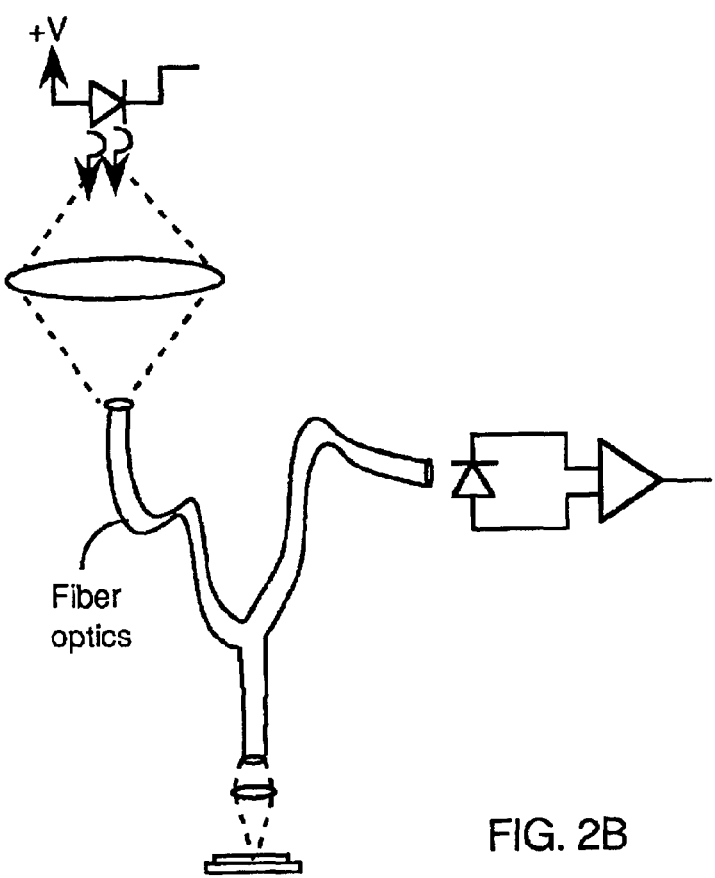
FIG. 2B for a different optical system implement with optical fibers for performing an ion implantation dose and/or energy measurement of the present invention.

Referring to FIG. 2B for a different embodiment of the present invention. Instead of using a beam splitter, optical fibers are used for transmitting the light signals. The difficulties in dealing with a same optical path for the reflected light and the illumination light is solved by using two sets of optical fibers, one transmits light from the light source and one transmits light to the detector. Lenses are used on both ends of the fiber bundles to optimize the amount of light transferred in and out of the fibers. The two bundles are joined into one bundle to produce a light path of the illumination light and reflected light that is again primarily the same path over the wafer surface.

Figure 2C:
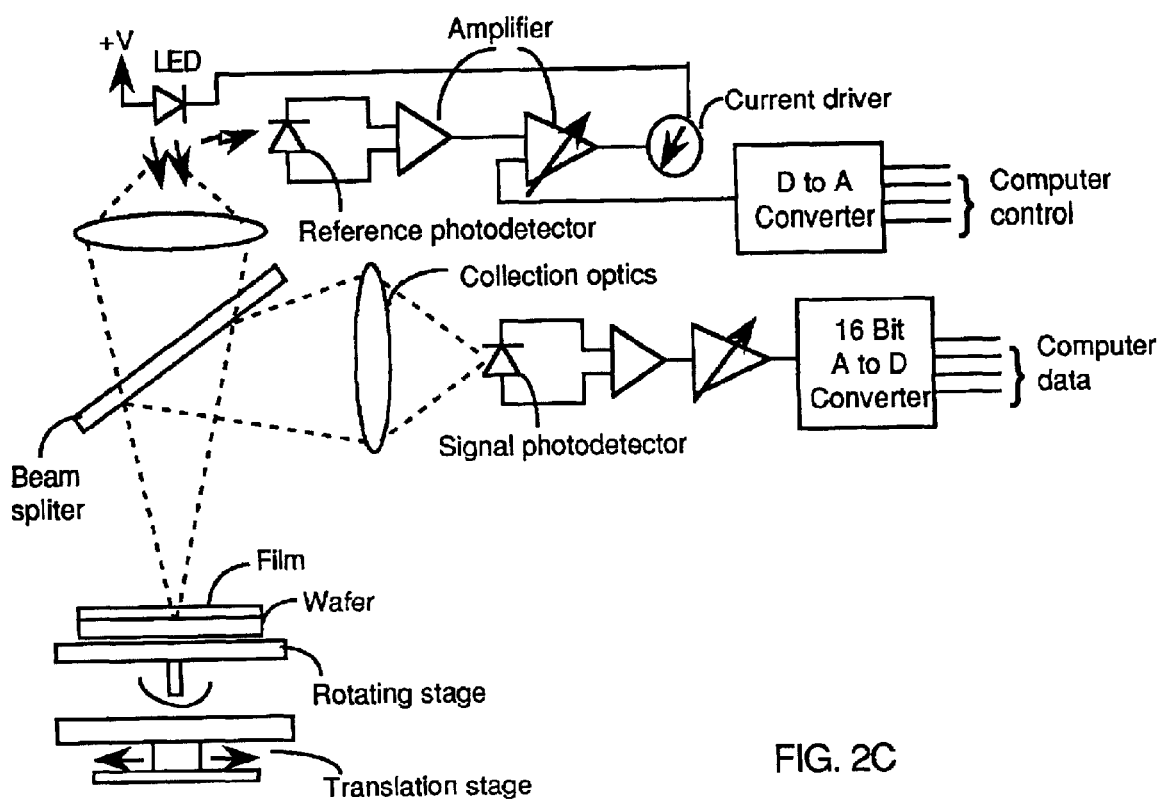
FIG. 2C is a diagram of a scanning densitometer implemented for reflection light measurements according to the method and techniques disclosed in this invention.

Referring to FIG. 2C for a diagram of the scanning densitometer implemented for reflection light measurements. A reference photodetector monitors the LED output and provides short-term feedback for stabilizing the light source. The Digital-to-Analog converter (D to A) allows the computer to set the LED current, hence light output needed to drive light intensity to the signal photodetector to a predetermined "full scale" when measuring the reference bare silicon sample.

According to above descriptions, an apparatus for measuring an ion-implantation dosage. The apparatus includes a scanning densitometer for measuring a reflected light from a monitor substrate. The apparatus further uses a monitor substrate. A thin film is supported on the monitor substrate wherein the thin film has an optical characteristic that is sensitive to the ion-implantation-dosage. The apparatus further includes a light source for projecting a measuring beam onto the monitor substrate for generating a reflected light. The apparatus also includes a bare silicon substrate for measuring a full scale reflected light represented by I0 reflected from the bare silicon substrate with the light source projecting a full scale light onto the bare silicon substrate. The apparatus further has a light source control means for controlling the light source to project the full scale light onto a plurality of points on the monitor substrate before and after an ion implantation for obtaining an implantation dosage profile. The apparatus further includes an ion-implantation dosage-measurement controller for controlling the apparatus and for calculating and reporting the optical density or color change and the implied implantation energy and/or dosage from the reflected light from the monitor substrate. In a preferred embodiment, the thin film has a reflectivity that is sensitive to the ion-implantation dosage and the energy of the ions. In another preferred embodiment, the thin film comprising a mixture of a dye with a weak covalent bond that is sensitive to the ion-implantation dosage and ion energy in a polymer matrix suitable for wafer-coating. This invention further discloses a monitor substrate for measuring an ion-implantation dosage. The monitor substrate further includes a thin film supported on the monitor substrate wherein the thin film having an optical characteristic that is sensitive to the ion-implantation -dosage and ion energy.

Figure 3A:
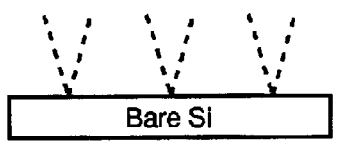
FIGS. 3A to 3D show the detail steps of implant dose and/or energy measurement procedures applying the measurement apparatus with the optically implant-sensitive layer of this invention.
Figure 3B:

The scanning technique utilizes an optical densitometer with a wavelength that matches the absorption of the dye after cleavage and a stage that allow the densitometer to view all points on the monitor wafer coated with the film at known, reproducible positions. The measurement is based on two scans of the monitor wafer: pre- and post-implantation. The optical density changes in the film can be determined and related to implant dose and/or energy by comparison with previously measured standards. Optical density of a film is defined as the logarithm base 10 of the ratio of the light intensity without the film to the light intensity passing through the film. Referring now to FIGS. 3A to 3D for the details of implant dose measurement procedures applying the measurement apparatus with the optically dose-sensitive layer of this invention. Referring to FIG. 3A, the process begins with a pre-scan reference step by focusing the densitometer on a bare silicon standard built into the system, adjust light intensity to reach a predetermined "full scale" amount of measured reflected light represented by $I_0$. In FIG. 3B, a pre-scan measurement process is performed over many measurement points over a monitor substrate. A layer of unexposed thin film 125-f implemented as optically implant-sensitive layer is coated over the monitor substrate. Measurement of the reflected light at a set of predetermined points on the monitor wafer is performed. The measurements resulted in reduced light intensities due to optical density of the unexposed film. The measured light intensities are represented by I'(1), I'(2), I'(3), . . . , I'(N) where I' represents the measurements are obtained from an unimplanted surface coated with a thin-film, N is the number of measurement.

Figure 3C:
Figure 3D:
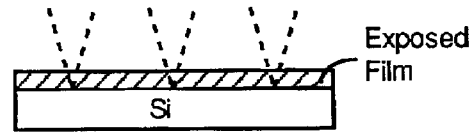

After the substrates shown in FIGS. 3A and 3B are implanted with ions, as shown in FIG. 3C, a post-scan reference measurement is made. Focusing a densitometer on a bare silicon reference, the light intensity is again adjusted to reach a predetermined "full scale" amount of measured reflected light, and again represented by $I_0$ as that defined in FIG. 3A. In FIG. 3D, a post scan measurement is carried out at multiple points same as the predetermined point measured in FIG. 3B on the monitor wafer formed with the optically dose-sensitive layer 125-f. The reflected light from the monitor wafer would have reduced light intensities due to the optical density of the exposed film. The intensities are represented by I"(1), I"(2), I'(3), . . . , I'(N), where the measurement points 1, 2, 3, . . . , N correspond to the same points used the measure the intensities I'. The change of the optical density at each of the measurement points is calculated to determine the effect of the film damage caused by the ion implantation. The change in optical density at point i the pre-implant optical density from the larger post-implant density. Since optical density is the logarithm of ratio of intensities, the calculation is carried out by taking the logarithm of the ratio of intensity difference ΔD(i) of reflected light before, i.e., D1(i), and after the ion implantation, i.e., D2(i). Specifically, the calculations are carried out for each of the measurement points i=1, 2, 3, . . . , N with the following equations:

$$\Delta D(i) = D2(i) - D1(i)$$
$$= \log[Io/I''(i)] - \log[Io/I'(i)]$$
$$= \log[I'(i)/I''(i)]$$

With the above calculations, a profile representing di, i.e., the dose of implantation, can be constructed with the calculated results of ΔD(i) for all the measurement points i=1, 2, 3, . . . , N.

As the optical density increases with both increasing dose and with increasing energy, a family of dose/energy curves needs to be constructed from known implants to provide dose information with a known implant energy. Alternately, if the implant dose is known the energy of implant can be estimated.

Optical density changes are by definition small numbers (usually expressed as floating point, or real numbers in computer programming jargon). Density changes can be more easily represented by a scaled density. For example, multiply the actual densities by a large number like 65,000 or $2^{16}$, and convert the result to an integer for computational ease. In order to reduce calculation times, one can also approximate optical density calculations by using only ratios or by simply subtracting intensities, rather than calculating the actual logarithms of intensity ratios.

By the ratio approximation:

$$\Delta D(i) = [Io - I''(i)]/[Io - I'(i)]$$

By the subtraction approximation:

$$\Delta D(i) = [Io - I''(i)] - [Io - I'(i)]$$
$$= I'(i) - I''(i)$$

The numerical values of the measurement results as described above can be provided directly to a computer for performing the above calculations and for presenting the composite of the calculated changes in optical density either numerically or pictorially. The variations measured for one monitor wafer are typically used to determine if the implant is uniform across the wafer within the wafer uniformity requirement. The mean of the optical density on a set of wafers obtained from the wafer-to-wafer uniformity measurements can be used to determine the drift over time in implant uniformity.

If the scanning is not made in a dark area, there may be ambient light adding to the total light in the path directed toward the detector. As optical detectors, such as photo-diodes and photomultipliers are wide band detectors, the majority of the background can be removed by adding a filter that passes only a small band of wavelengths that include the wavelengths used by the densitometer.

Figure 4A:
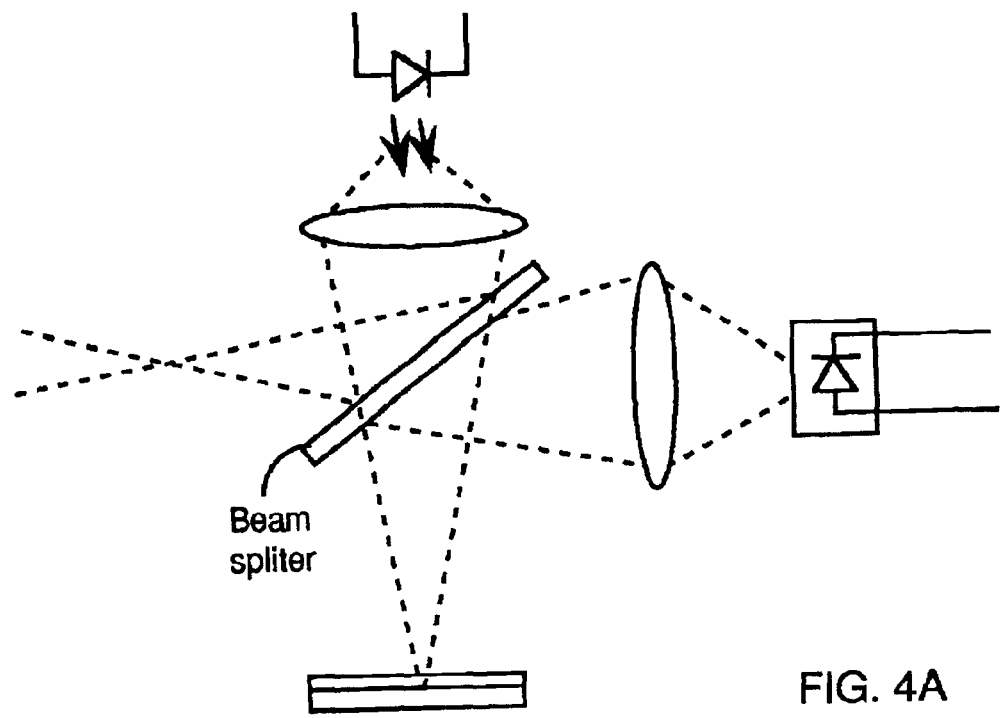
FIGS. 4A and 4B are functional diagrams showing alternating measurement positions.
Figure 4B:
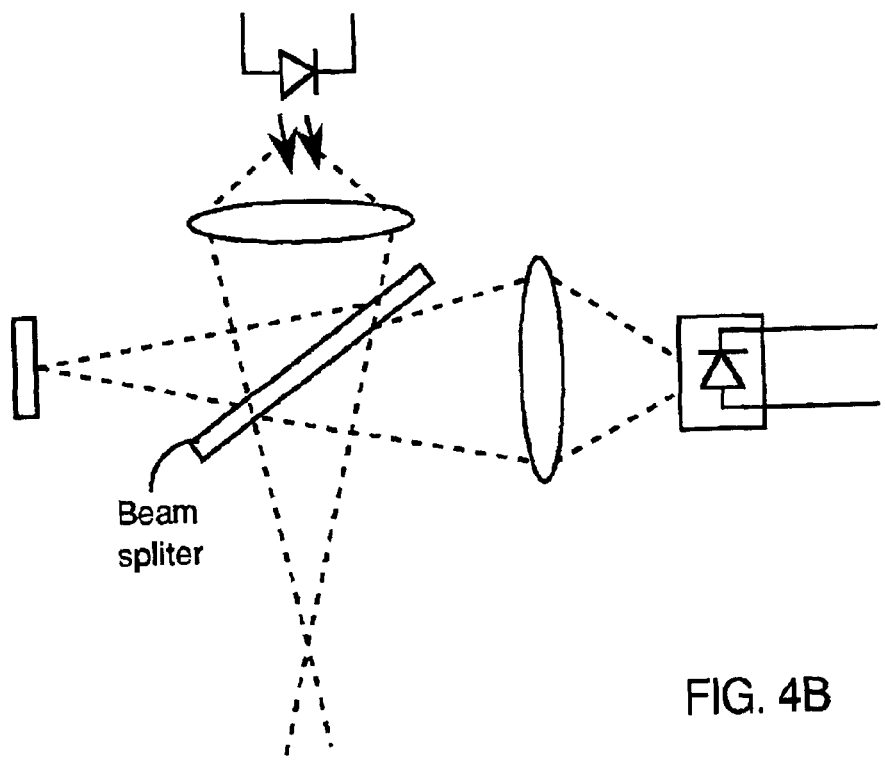

The use of the reference measurements as described above in FIGS. 3A to 3D is important to this measurement technique. The bare silicon wafer implemented for reference measurements can be placed on the stage next to the wafer to be measured. It can also be placed elsewhere in the optical path. As shown in FIG. 4, the action of the beam splitter 120 is to reflect 50% of the incident light and transmit 50%. Thus half of the light from the illumination optics is reflected out of the beam path and is typically absorbed by a non-reflecting surface to prevent any effects on the measurement. According to FIGS. 4B and 4B, there are two measurement positions, and reflections from either the focal point at the left or at the bottom will have the same measurement effect. The reference sample can be measured by placing the reference silicon wafer at the left focal point while removing the wafer and preventing light from reflecting from the bottom focal point by placing a non-reflecting surface under the optics or allow the beam to transmit to infinity. The bare silicon wafer as reference measurement sample can be held at the focal position and a shutter placed in front of the reference that is closed unless the reference wafer is being measured. Alternately, the reference silicon wafer can be kept out of the beam path normally and inserted when a reference measurement is required.

According to above descriptions, a method for measuring an ion-implantation energy and dosage is disclosed in this invention. The method includes a step a) measuring a full-scale reflection, represented by Io, by projecting a full-scale light onto a bare silicon. The method further includes a step b) performing a pre-scan reflection measurement by projecting the full scale light onto a plurality of points on a monitor substrate having a thin film supported on the monitor substrate with the thin film having an optical characteristic that is sensitive to the ion-implantation energy-dosage. And, the step further includes a step c) performing an ion implantation and then performing a post-scan reflection measurement by projecting the full scale light onto the plurality of points on the monitor substrate. A reflection intensity difference for each of the points on the monitor substrate is measured. The difference of reflection intensity for each point is then used for calculating an ion-implantation energy-dosage profile. In a preferred embodiment, the step c) of obtaining a set of reflection intensity difference for each of the plurality of point on the monitor substrate is a step of calculating a logarithmic value for a ratio of a reflection intensity before and after the step of ion implantation.

In essence, this invention discloses a method for measuring an ion-implantation dosage at a known implanting ion energy or measuring an implanting ion energy if the dosage is known. The method includes a step of forming a thin film with an optical characteristic sensitive to an ion-implantation energy-dosage. The method further includes a step of measuring a change of the optical characteristic after an ion implantation for calculating the ion-implantation energy or dosage.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

We claim:

1. A monitor subtrate for measuring an ion-implantation ion energy and dosage comprising:
   a thin film supported on said monitor substrate wherein said thin film having a reflectivity sensitive to said ion-implantation damage; and
   said thin film comprising a mixture of dye molecules with weak covalent bonds sensitive to said ion-inplantation energy and dosage in a polymer matrix suitable for wafer-coating; and
   said mixture of a dye with a weak covalent bond having a heterogeneous-cleavage property that is sensitive to said ion-implantation energy and dosage.

2. The substrate of claim 1 wherein:
   said dye mixture has an optical property of changing from transparent to colored upon heterogenious-cleavage.

3. The substrate of claim 1 wherein:
   said monitor substrate is a silicon substrate, which may have a thin oxide coating.

4. The substrate of claim 1 wherein:
   said thin film having a thickness ranging substantially from one micrometer to twenty micrometers.

5. An apparatus for measuring an ion-implantation dosage comprising:
   a scanning densitometer for measuring reflected light from a monitor substrate;
   a thin film supported on said monitor substrate wherein said thin film having an optical characteristic sensitive to said ion-implantation;
   a light source for projecting a measuring beam onto said monitor substrate for generating a reflected light; and
   a bare silicon substrate for measuring a full scale reflected light represented by I0 reflected from said bare silicon substrate with said light source projecting a full scale light onto said bare silicon substrate.

6. The apparatus of claim 5 further comprising:
   a light source control means for controlling said light source to project said full scale light onto a plurality of points on said monitor substrate before and after an ion implantation for obtaining reflectances I' and I" respectively at each point.

7. The apparatus of claim 5 further comprising:
   an ion-implantation measurement controller for controlling said apparatus and for calculating said implantation ion energies and dosage from said reflected light from said monitor substrate.

8. The apparatus of claim 5 wherein:

said thin film having a reflectivity that is sensitive to said ion-implantation ion energy and dosage.

9. The apparatus of claim 5 wherein:

said thin film comprising a mixture of a dye with a weak covalent bond that is sensitive to said ion-implantation damage and a polymer matrix suitable for wafer-coating.

10. The apparatus of claim 9 wherein:

said mixture of a dye with a weak covalent bond having a heterogeneous-cleavage property that is sensitive to said ion-implantation ion energy and dosage.

11. The apparatus of claim 5 wherein:

said monitor substrate is a silicon substrate.

12. The apparatus of claim 5 wherein:

said monitor substrate is a silicon substrate with a thin oxide coating of 50 to 5000 angstroms.

13. The apparatus of claim 5 wherein:

said thin film having a thickness ranging substantially from a micrometer to twenty micrometers.

14. A method for measuring an ion-implantation ion energy and/or dosage comprising:

a) measuring a full scale reflection, represented by Io, by projecting a full scale light onto a bare silicon;

b) performing a pre-implant reflection measurement by projecting said full scale light onto a plurality of points on a monitor substrate having a thin film supported on said monitor subtrate with said thin film having an optical characteristic that is sensitive to said ion-implantation-dosage producing optical intensities I'; and c) performing an ion implantation and then performing a post-implant reflection measurement by projecting said full scale light onto said plurality of points on said monitor substrate to obtain a set of reflection intensities, I", for each of said points on said monitor substrate for calculating an ion-implantation energy and/or dosage profile.

15. The method of claim 14 wherein:

said step c) of obtaining a set of reflection intensity differences for each of said plurality of point on said monitor substrate is a step of calculating a logarithmic value for a ratio of I', a reflection intensity before, and I", a reflection intensity after said step of ion implantation.

16. The method of claim 14 wherein:

said step c) of obtaining a set of reflection intensity differences for each of said plurality of point on said monitor substrate is a step of calculating a ratio of a reflection intensities before and after said step of ion implantation.

17. The method of claim 14 wherein:

said step c) of obtaining a set of reflection intensity differences for each of said plurality of point on said monitor substrate is a step of calculating the arithmetic differences between reflection intensities before and after said step of ion implantation.

* * * * *